(12) United States Patent
Schnittger et al.

(10) Patent No.: US 8,956,624 B2
(45) Date of Patent: Feb. 17, 2015

(54) **COMPOSITIONS AND METHODS FOR TREATING SKIN WITH EXTRACT FROM *TRAMETES***

(75) Inventors: Steven F. Schnittger, Huntington, NY (US); Daniel H. Maes, Huntington, NY (US); Michael Sullivan, Holbrook, NY (US)

(73) Assignee: ELC Management, LLC, New York, NY (US)

( * ) Notice: Subject to any disclaimer, the term of this patent is extended or adjusted under 35 U.S.C. 154(b) by 0 days.

(21) Appl. No.: 12/306,372

(22) PCT Filed: Nov. 21, 2008

(86) PCT No.: PCT/US2008/084373
§ 371 (c)(1),
(2), (4) Date: Apr. 15, 2010

(87) PCT Pub. No.: WO2009/085472
PCT Pub. Date: Jul. 9, 2009

(65) Prior Publication Data
US 2010/0203077 A1 Aug. 12, 2010

Related U.S. Application Data

(60) Provisional application No. 61/014,837, filed on Dec. 19, 2007.

(51) Int. Cl.
*A61K 36/07* (2006.01)
*A61Q 19/00* (2006.01)
*A61K 8/97* (2006.01)
*A61Q 19/02* (2006.01)

(52) U.S. Cl.
CPC ............ *A61Q 19/00* (2013.01); *A61K 8/975* (2013.01); *A61Q 19/02* (2013.01)
USPC .................... 424/195.15; 424/401

(58) Field of Classification Search
None
See application file for complete search history.

(56) References Cited

U.S. PATENT DOCUMENTS

| | | | |
|---|---|---|---|
| 3,215,724 A | 11/1965 | Strobel et al. | |
| 3,439,088 A | 4/1969 | Edman | |
| 3,781,417 A | 12/1973 | Welter et al. | |
| 3,818,105 A | 6/1974 | Coopersmith et al. | |
| 4,803,067 A | 2/1989 | Brunetta et al. | |
| 4,970,252 A | 11/1990 | Sakuta et al. | |
| 5,118,496 A | 6/1992 | Herstein | |
| 5,183,588 A | 2/1993 | Salerno et al. | |
| 5,183,589 A | 2/1993 | Brunetta et al. | |
| 5,219,838 A * | 6/1993 | Tomita et al. ............... | 514/18.6 |
| 5,236,986 A | 8/1993 | Sakuta | |
| 5,412,004 A | 5/1995 | Tachibana et al. | |
| 5,654,362 A | 8/1997 | Schulz, Jr. et al. | |
| 5,760,116 A | 6/1998 | Kilgour et al. | |
| 5,811,487 A | 9/1998 | Schulz, Jr. et al. | |
| 5,837,793 A | 11/1998 | Harashima et al. | |
| 5,843,193 A | 12/1998 | Hawkins et al. | |
| 6,599,328 B1 | 7/2003 | Plos et al. | |
| 6,986,895 B2 | 1/2006 | Suares et al. | |
| 2002/0034488 A1 | 3/2002 | Kravtchenko et al. | |
| 2004/0025265 A1 | 2/2004 | Lang et al. | |
| 2004/0241133 A1 | 12/2004 | Akiyama et al. | |
| 2006/0034875 A1 | 2/2006 | Nakanishi et al. | |
| 2007/0224229 A1 | 9/2007 | Gibbons et al. | |

FOREIGN PATENT DOCUMENTS

| | | |
|---|---|---|
| EP | 1158021 | 11/2001 |
| EP | 1918363 | 5/2008 |
| GB | 1390541 | 4/1975 |
| GB | 1390542 | 4/1975 |
| JP | 60-045531 | 3/1985 |
| JP | 61018708 | 1/1986 |
| JP | 61-18708 | 4/1994 |
| JP | 07010734 A  * | 1/1995 |
| JP | 08-070862 | 3/1996 |
| JP | 11-060495 | 3/1999 |
| JP | 2001-342125 | 12/2001 |
| JP | 2003-252748 A  * | 9/2003 |
| JP | 2003-267855 | 9/2003 |
| JP | 2004-224702 | 8/2004 |
| JP | 2004-277340 | 10/2004 |
| JP | 2004-315512 | 11/2004 |
| JP | 2005-239644 | 9/2005 |
| JP | 2006-117534 | 5/2006 |
| JP | 2006-124386 | 5/2006 |
| JP | 2006-290749 | 10/2006 |
| JP | 2006-527166 | 11/2006 |

(Continued)

OTHER PUBLICATIONS http://www.gnpd.com/sinatra/gnpd/search_results/&item_id=10095255; Mintel gnpd; Collagen 5 Intensive Eye Repair; Record ID: 10095255; University Medical Products; Face Lift; Skincare; Eye Care; USA; Oct. 2001.*
http://www.mushroomexpert.com/trametes_hirsuta.html—accessed Apr. 2014.*
English translation of Morimura (JP 2005-239644); 2005.*
http://www.coolasuncare.com/sun-science/uva-vs-uvb—accessed Apr. 2014.*
http.//www.gnpd.com; Mintel gnpd; Face Lift Cream; Record ID: 10068795; University Medical Products; University Medical; Skincare; Face/Neck Care; Canada; Jul. 2000.

(Continued)

*Primary Examiner* — Susan Hoffman
(74) *Attorney, Agent, or Firm* — Julie M. Blackburn

(57) ABSTRACT

Compositions for treating skin containing at least one extract from the genus *Trametes* and at least one viscosity enhancing synthetic polymer, and methods for whitening skin, treating skin for improvement, or treating skin disorders associated with pigmentation such as uneven pigmentation, skin mottling, or age spots or other dermatological disorders such as eczema, rosacea, hyperkeratinization, and so on.

18 Claims, 1 Drawing Sheet

(56) References Cited

FOREIGN PATENT DOCUMENTS

| JP | 2006-327988 | | 12/2006 |
|---|---|---|---|
| JP | 2006-342098 | | 12/2006 |
| KR | 2001-0114117 | | 12/2001 |
| KR | 10-2005-0068068 | * | 7/2005 |
| WO | WO 98/17274 A1 | * | 4/1998 |
| WO | WO2004/024798 | | 3/2004 |
| WO | WO-2005-004830 | | 1/2005 |
| WO | WO2007/013588 | | 2/2007 |

OTHER PUBLICATIONS http://www.gnpd.com; Mintel gnpd; Anti-Thinning Hair Care Products; Record ID: 10062463; University Medical Products; More Hair; Haircare; Hair Treatments; USA; Sep. 1999.

http://www.gnpd.com/sinatra/gnpd/search_results/&item_id=542875; Mintel gnpd; Thinning Hair Treatment; Record ID: 542875; University Medical Products USA; More Hair; Haircare; Hair Treatments; USA; Jun. 2006.

http://www.gnpd.com/sinatra/gnpd/search_results/&item_id=10095255; Mintel gnpd; Collagen 5 Intensive Eye Repair; Record ID: 10095255; Universtiy Medical Products; Face Lift; Skincare; Eye Care; USA; Oct. 2001.

http://www.mushroomexpert.com/trametes_versicolor.html; MushroomExpert.com; Michael Kuo; Trametes versicolor: The Turkey Tail; pp. 1-3; Dec. 11, 2007.

http://stnweb.cas.org/cgi-bin/sdcgi?SID=237244-0991577223-200&APP=stnweb&; Eggensperger, H.; Wilker, Michelle; Verlag fuer Chemische Industrie Journal; Multiactive polysaccharides; Part 1; Fungi Extracts; vol. 123(8) pp. 542-546; 1997.

PCT International Search Report; International Application No. PCT/U808/084373; Completion Date: May 21, 2009; Date of Mailing: May 22, 2009.

PCT Written Opinion of the International Searching Authority, or the Declaration; International Application No. PCT/US08/084373; Completion Date: May 21, 2009; Mailing Date: May 22, 2009.

Supplementary European Search Report; EP08866075; Completion Date: Dec. 4, 2012; Date of Mailing: Dec. 19, 2012.

* cited by examiner

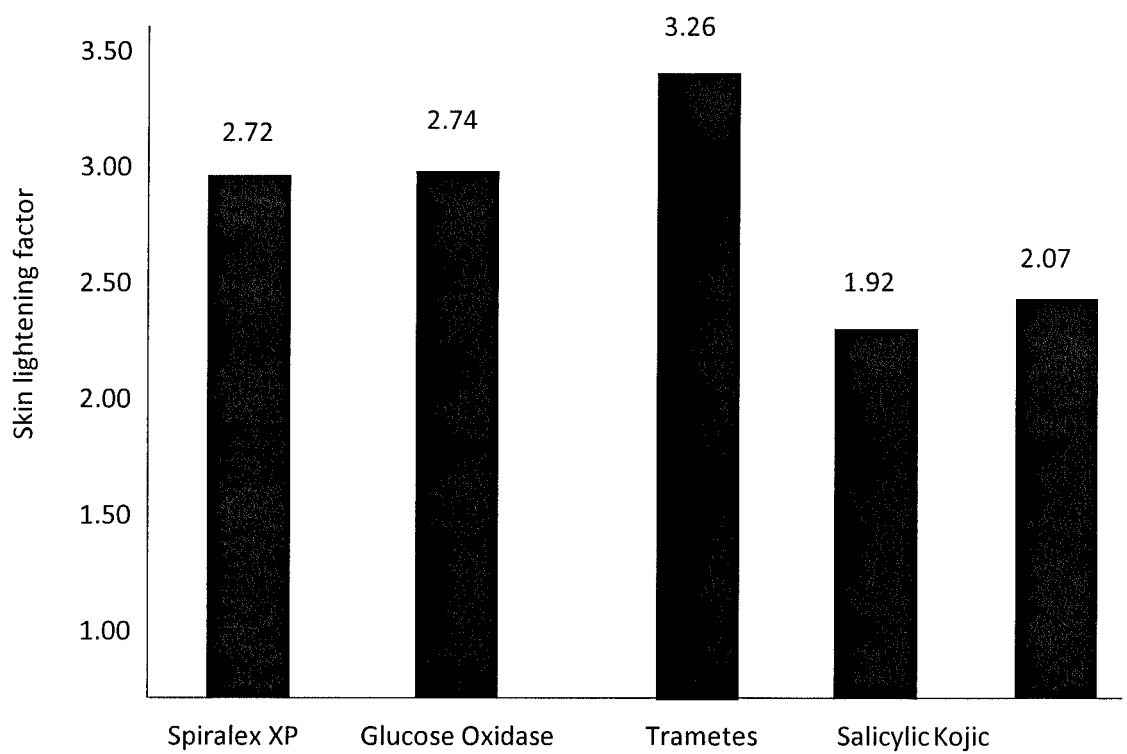

COMPOSITIONS AND METHODS FOR TREATING SKIN WITH EXTRACT FROM *TRAMETES*

This application is a national stage filing of PCT/US2008/084373, filed Nov. 21, 2008, and claims priority from U.S. 61/014,837, filed Dec. 19, 2007.

TECHNICAL FIELD

The invention is in the field of methods and compositions for treating skin for improvement.

BACKGROUND OF THE INVENTION

Cosmetics companies are always looking for new ingredients that provide beneficial properties to skin. Extracts of plants are well known for use in cosmetics. Plant extracts contain many different types of organic compounds that are very beneficial to skin. Certain disciplines such as traditional Chinese medicine and herbology are based upon the principles of using natural plant extracts to treat various skin and bodily ailments.

However, as beneficial as such plant extracts may be to skin, they are not without complications when it comes to formulation. Sometimes such extracts will "brown" a formula, that is, the extract contains components that oxidize in air to turn a formula a commercially unacceptable tan or brown shade. In other cases, such extracts may be unstable and degrade to various sub-components that are no longer efficacious in providing the desired end benefit. Accordingly, formulation of commercially acceptable cosmetic products that provide the aesthetics that demanding consumers require is not an easy feat.

Extracts of fungi, in particular, are often desired for use in cosmetics. Such extracts have many beneficial properties to skin. For example, fungi from the genus *Trametes* are known for their medicinal properties. Sophisticated outdoorsmen will sometimes chew a piece of fungi picked from *Trametes Versicolor* (also referred to as Turkey Tail) like gum when they are hiking in the woods.

However, it has been discovered that in addition to its perceived medicinal properties, extracts from the genus *Trametes* also have beneficial properties when applied skin. For example, *Trametes* extracts contain certain subcomponents that whiten or brighten skin by inhibiting tyrosinase or affecting other mechanisms that contribute to skin pigmentation, or otherwise improving the appearance of uneven pigmentation, for example, like that found in age spots or mottled skin. Extracts from the *Trametes* genus are also excellent moisturizers, and some species may also be useful in absorbing excess sebum in oily skinned individuals. However, because *Trametes* extracts can be difficult to formulate with, and cosmetics consumers have high demands when it comes to aesthetics and stability of their products, it is necessary to develop certain cosmetic base formulations that are capable of maintaining the stability and efficacy of the *Trametes* extract in the cosmetic formula and providing aesthetically pleasing commercially acceptable cosmetic products.

It has been discovered that incorporating the *Trametes* extract into a composition containing a synthetic polymeric viscosity enhancing agent provides a stable cosmetic formulation that is aesthetically pleasing.

It is an object of the invention to provide a topical cosmetic or pharmaceutical composition comprising at least one extract of *Trametes* and at least one viscosity enhancing synthetic polymer.

It is a further object of the invention to provide a topical cosmetic or pharmaceutical emulsion composition comprising at least one extract of *Trametes* and at least one viscosity enhancing synthetic polymer.

It is a further object of the invention to provide a method for treating skin for improvement comprising applying to the skin a topical cosmetic or pharmaceutical composition comprising at least one extract of *Trametes* and at least one viscosity enhancing synthetic polymer.

It is a further object of the invention to provide a method for whitening skin comprising applying to the skin a topical cosmetic or pharmaceutical composition comprising at least one extract of *Trametes* in an amount sufficient to whiten skin, and at least one viscosity enhancing synthetic polymer.

SUMMARY OF THE INVENTION

The invention comprises a topical cosmetic or pharmaceutical composition comprising at least one extract from the genus *Trametes* and at least one viscosity enhancing synthetic polymer. The invention also comprises a topical cosmetic or pharmaceutical emulsion composition comprising at least one extract from the genus *Trametes* and at least one viscosity enhancing synthetic polymer.

The invention also comprises a method for treating skin for improvement comprising applying to the skin a topical cosmetic or pharmaceutical composition comprising at least one extract from the genus *Trametes* and at least one viscosity enhancing synthetic polymer.

The invention also comprises a method for whitening skin comprising applying to the skin a topical cosmetic or pharmaceutical composition comprising at least one extract from the genus *Trametes* and at least one viscosity enhancing synthetic polymer.

The invention also comprises a method for treating uneven pigmentation, age spots, mottled pigmentation, roseacea, or other pigmentation disorders in skin comprising applying to the skin a topical cosmetic or pharmaceutical composition comprising at least one extract from the genus *Trametes* and at least one viscosity enhancing synthetic polymer.

DESCRIPTION OF DRAWINGS

FIG. 1 is a graph depicting the skin lightening factor results in testing of various ingredients.

DETAILED DESCRIPTION

The compositions of the invention may be in the anhydrous, emulsion, solution, suspension, or gel form. If aqueous based, the compositions may comprise from about 0.1-99%, preferably from about 0.5 to 90%, more preferably from about 1-85% water. If in the emulsion form, in addition to these amounts of water, the composition may comprise from about 0.1-99%, preferably from about 0.5-95%, more preferably from about 1-90% of oil. All percentages mentioned herein are percentages by weight unless otherwise indicated.

I. *Trametes* Extract

The composition comprises at least one extract of a fungi from the genus *Trametes* (formerly known as *Coriolus*). Examples of various species that belong to the genus *Trametes* include *Trametes Versicolor, Trametes Pubescens, Trametes Hirsuta, Trametes Ochracea, Trametes Elegans, Trametes Colliculosa, Trametes Gibbosa, Trametes Palustris, Trametes Villosa, Trametes Suaveolens, Trametes Cervina, Trametes Cingulata*, and so on. Particularly preferred is an extract from *Trametes Versicolor*. The extract may be obtained by simple extraction of the fungi with solvents such as alkanols (ethanol, propanol), water, or other volatile organic solvents such as benzyl alcohol, lower alkyl acetates, and so on. Alternatively, the fungi can be mashed or pulverized, diluted in water, and strained through sieves having various pore sizes to produce a suitable extract. The extract may also be in the freeze dried or minced form. The extract may also be purchased from various vendors such as the VTT Technical Research Center of Finland, specifically VTT Biotechnology Culture Collection, Vuorimiehentle, Finland. The *Trametes* extract may be present in the composition ranging from about 0.00001 to 40%, preferably from about 0.00005 to 35%, more preferably from about 0.0001 to 30%.

II. The Viscosity Enhancing Synthetic Polymer

The viscosity enhancing synthetic polymer is a formula stabilizing polymer that stabilizes the formula containing the *Trametes* extract and enhances the delivery of active ingredients to the skin. The term "viscosity enhancing" means that the synthetic polymer will increase the viscosity of the composition. This viscosity increase may be non-thixotropic or thixotropic. If thixotropic, the viscosity of the composition will be greater in the resting state, and the viscosity will be reduced when exposed to shear force. The term "synthetic" means that the polymer is synthesized, not naturally occurring. The viscosity enhancing synthetic polymer may be comprised of organic or silicone monomers, or combinations thereof, and may also have film forming properties. It may be solubilized or dispersed in the aqueous phase if the composition of the invention contains water, or in the oil phase. If the composition of the invention is anhydrous, the viscosity enhancing synthetic polymer may be found in the oil phase of the composition. The polymer may be present in the composition ranging from about 0.001 to 80%, preferably from about 0.005 to 75%, more preferably from about 0.01 to 65%. Suitable viscosity enhancing synthetic polymers include, but are not limited to those set forth below:

A. Polymers and Copolymers from Organic Monomers

Viscosity enhancing synthetic polymers suitable for use in the compositions of the invention may comprise homo- or copolymers of organic groups such as acrylic acid, methacrylic acid or their simple esters (esters formed from alcohols having, for example, 1, 2, 3, 4, 5, 6, 7, 8, 9, 10, 12, 14, 16, 18, 22, or 24 carbon atoms which may be in the form of a straight or branched alkyl chain). Examples include methyl, ethyl, propyl, butyl, pentyl, hexyl, pentyl, octyl, nonyl, deca, dodeca, cetyl, lauryl, stearyl, behenyl, methacrylate or acrylate monomers (e.g. methyl methacrylate, methyl acrylate, ethyl methacrylate, ethyl acrylate, behenyl acrylate, lauryl acrylate, and so on).

Suitable viscosity enhancing polymers may be either homopolymers of acrylamide or copolymers of acrylamide and one or more simple alkyl derivatives thereof such as methyl acrylamide, ethyl acrylamide, and so on. In this case the polymer is referred to as acrylamides copolymer. The acrylamide monomer may also form a component of more complex viscosity enhancing synthetic polymer.

Acryloyldimethyltaurate monomers may also form a component of the viscosity enhancing synthetic polymer.

The viscosity enhancing film forming polymer may also contain vinyl, acetate, or vinyl pyrrolidone monomers.

The organic based viscosity enhancing synthetic polymer may also contain various types of organic moieties such as saturated or unsaturated fatty carboxylic acids having 4 to 22 carbon atoms. Examples of saturated fatty carboxylic acids that may be copolymerized include butyric (C4), caproic (C6), caprylic (C8), capric (C 10), lauric (C 12), myristic (C 14), palmitic (C16), stearic (C18), arachidic (C20), or behenic (C22). Examples of unsaturated fatty acids that may be copolymerized with the other monomers mentioned herein include myristoleic, palmitoleic, oleic, linoleic, alpha linolenic, arachidonic, eicosapentaenic, or erucic, or docosahexanoic acids. Dicarboxylic acids having from 2 to 30 carbon atoms are also suitable such as adipic acid, itaconic acid, oxalic, malonic, succinic, glutaric, pimelic, subaric, azaleic, sebacic, and so one.

Examples of alkylene oxides that may be polymerized with other monomers mentioned herein or with themselves include those having alkyl groups of 1-30 carbon atoms with repeating alkylene oxide units ranging from about 2 to 500; for example Laureth 2-500 (wherein the designation 2-500 refers to the number of repeating ethylene oxide moieties), Ceteth 2-500, Steareth 2-500, Palmeth 2-500, Beheneth 2-500 and so on. Other examples or organic groups that may be polymerized include alpha hydroxy acids or derivatives thereof such as citric, glycolic, malic, itaconic, lactic, malic, tartaric acids, or ketone derivatives thereof such as glucono-lactone, lactone, and so on.

The viscosity enhancing synthetic polymer may be neutralized with alkali or alkaline earth metal salts such as sodium, potassium, or ammonium.

A wide variety of viscosity enhancing organic polymers may be used to thicken and stabilize the compositions of the invention. Further specific examples include, but are not limited to polymers sold by Clariant Corporation under the trademark Aristoflex, including Aristoflex AVC which is ammonium acryloyldimethyltaurate/VP copolymer; Aristoflex AVC-1 which is Aristoflex HMB which is Ammonium Acryloyldimethyltaurate/Beheneth-25 Methacrylate Crosspolymer; Aristoflex SNC, which is Ammonium Acryloyldimethyltaurate/Steareth-8 Methacrylate Copolymer; and so on. Other examples of commercial polymers that may be used include those sold by Lamberti SpA under the Viscolam trademark, including Viscolam BMC25, which is Acrylates/Beheneth-25 Methacrylate Copolymer; Viscolam MAC7, which is Acrylates Copolymer; Viscolam AT64, a mixture of Sodium Acrylate/Sodium Acryloyldimethyl Taurate Copolymer, mineral oil, and laureth-8; Viscolam AT 64P, a mixture of Sodium Acrylate/Sodium Acryloyldimethyl Taurate CopolymerSodium Acrylate/Sodium Acryloyldimethyl Taurate Copolymer, polydecene and laureth-8; Viscolam AT 100P, which is a mixture of Sodium Polyacryloyldimethyl Taurate, hydrogenated polydecene, and trideceth-10; and Viscolam C, which is a mixture of Acrylates Copolymer and Steareth-20; and so on. Also suitable are polymers sold under the Simulgel trademark by SEPPIC, such as Simulgel 600, which is Acrylamide/Sodium Acryloyldimethyltaurate Copolymer; Simulgel 800, which is Sodium Polyacryloyldimethyl Taurate Copolymer; Simulgel A, which is a mixture of ammonium polyacrylate, isohexadecane, and PEG-40 castor oil; Simulgel EG, which is a mixture of Sodium Acrylate/Sodium Acryloyldimethyl Taurate Copolymer, isohexadecane, and Polysorbate-80; Simulgel EG, which is a mixture of Sodium Acrylate/Sodium Acryloyldimethyl Taurate Copolymer, isohexadecane, and Polysorbate-80; Simulgel EPG, which is a mixture of Sodium Acrylate/Sodium Acryloyldimethyl Taurate Copolymer, polyisobutene, and caprylyl/capryl glucoside; Simulgel FL, which is a mixture of Hydroxyethyl Acrylate/Sodium Acryloyldimethyl Taurate Copolymer, isohexadecane, and Polysorbate 60; Simulgel I-S 100, which is a mixture of Hydroxyethyl Acrylate/Sodium Acryloyldimethyl Taurate Copolymer, isohexadecane, and Polysorbate 60; and Simulgel NS, which is a mixture of Hydroxyethyl Acrylate/Sodium Acryloyldimethyl Taurate Copolymer, squalane, and Polysorbate-60. Also suitable are synthetic viscosity enhancing polymers sold under the Carbopol designation, such as Carbopol 907 having the INCI name polyacrylic acid; Carbopol 910 having the INCI name Carbomer; Carbopol Aqua CC Polymer, having the INCI name Polyacrylate-1 crosspolymer; Carbopol SF-1 Polymer, having the INCI name Acrylates Copolymer; Carbopol EDT 2020 Polymer, having the INCI name Acrylates/C10-30 Alkyl Acrylate Crosspolymer; Carbopol EDT 2050 Polymer, and Carbomers 940, 941, 954, 980, 2984, 5984, 934P, Ultrez 10, and 981, all having the INCI name Carbomer; Carbopol 1342, 1382, Ultrez 20, and Ultrex 21, all having the INCI name Acrylates/C10-30 Alkyl Acrylate Crosspolymer. Other polymers include those sold by Finetex under the Octacare tradename, or sold by Sensient under the Covacryl tradename, such as Octacare RM 100 and Covacryl AC or ADS, all of which have the INCI name Sodium Polyacrylate; Octacare RM 110, which has the INCI name Acrylamide/Sodium Acrylate copolymer; Octacare X100 or X110, both of which have the INCI name Sodium Polyacrylate. Also suitable are similar types of polymers sold under the Covacryl tradename by Sensient Corporation, such as Covacryl VIP, which has the INCI name Ammonium Polyacrylate.

B. Silicone Based Viscosity Enhancing Synthetic Polymers

1. Nonemulsifying Silicone Elastomers

Also suitable as formula stabilizing viscosity enhancing synthetic polymers for the *Trametes*-containing compositions are various types of silicone elastomers. Such silicone elastomers generally include those that are formed by addition reaction-curing, by reacting an SiH-containing diorganosiloxane and an organopolysiloxane having terminal olefinic unsaturation, or an alpha-omega diene hydrocarbon, in the presence of a platinum metal catalyst. Such elastomers may also be formed by other reaction methods such as condensation-curing organopolysiloxane compositions in the presence of an organotin compound via a dehydrogenation reaction between hydroxyl-terminated diorganopolysiloxane and SiH-containing diorganopolysiloxane or alpha omega diene; or by condensation-curing organopolysiloxane compositions in the presence of an organotin compound or a titanate ester using a condensation reaction between an hydroxyl-terminated diorganopolysiloxane and a hydrolysable organosiloxane; peroxide-curing organopolysiloxane compositions which thermally cure in the presence of an organoperoxide catalyst.

One type of elastomer that may be suitable is prepared by addition reaction-curing an organopolysiloxane having at least 2 lower alkenyl groups in each molecule or an alpha-omega diene; and an organopolysiloxane having at least 2 silicon-bonded hydrogen atoms in each molecule; and a platinum-type catalyst. While the lower alkenyl groups such as vinyl, can be present at any position in the molecule, terminal olefinic unsaturation on one or both molecular terminals is preferred. The molecular structure of this component may be straight chain, branched straight chain, cyclic, or network. These organopolysiloxanes are exemplified by methylvinylsiloxanes, methylvinylsiloxane-dimethylsiloxane copolymers, dimethylvinylsiloxy-terminated dimethylpolysiloxanes, dimethylvinylsiloxy-terminated dimethylsiloxane-methylphenylsiloxane copolymers, dimethylvinylsiloxy-terminated dimethylsiloxane-diphenylsiloxane-methylvinylsiloxane copolymers, trimethylsiloxy-terminated dimethylsiloxane-methylvinylsiloxane copolymers, trimethylsiloxy-terminated dimethylsiloxane-methylphenylsiloxane-methylvinylsiloxane copolymers, dimethylvinylsiloxy-terminated methyl(3,3,3-trifluoropropyl)polysiloxanes, and dimethylvinylsiloxy-terminated dimethylsiloxane-methyl(3,3,-trifluoropropyl)siloxane copolymers, decadiene, octadiene, heptadiene, hexadiene, pentadiene, or tetradiene, or tridiene.

Curing proceeds by the addition reaction of the silicon-bonded hydrogen atoms in the dimethyl methylhydrogen siloxane, with the siloxane or alpha-omega diene under catalysis using the catalyst mentioned herein. To form a highly crosslinked structure, the methyl hydrogen siloxane must contain at least 2 silicon-bonded hydrogen atoms in each molecule in order to optimize function as a crosslinker.

The catalyst used in the addition reaction of silicon-bonded hydrogen atoms and alkenyl groups, and is concretely exemplified by chloroplatinic acid, possibly dissolved in an alcohol or ketone and this solution optionally aged, chloroplatinic acid-olefin complexes, chloroplatinic acid-alkenylsiloxane complexes, chloroplatinic acid-diketone complexes, platinum black, and carrier-supported platinum.

Suitable silicone elastomers for use as viscosity enhancing synthetic polymers in the compositions of the invention may be in the powder form, or dispersed or solubilized in solvents such as water, volatile or non-volatile silicones, or silicone compatible vehicles such as paraffinic hydrocarbons or esters. Examples of silicone elastomer powders include vinyl dimethicone/methicone silesquioxane crosspolymers like Shin-Etsu's KSP-100, KSP-101, KSP-102, KSP-103, KSP-104, KSP-105, hybrid silicone powders that contain a fluoroalkyl group like Shin-Etsu's KSP-200 which is a fluorosilicone elastomer, and hybrid silicone powders that contain a phenyl group such as Shin-Etsu's KSP-300, which is a phenyl substituted silicone elastomer; and Dow Corning's DC 9506. Examples of silicone elastomer powders dispersed in a silicone compatible vehicle include dimethicone/vinyl dimethicone crosspolymers supplied by a variety of suppliers including Dow Corning Corporation under the tradenames 9040 or 9041, GE Silicones under the tradename SFE 839, or Shin-Etsu Silicones under the tradenames KSG-15, 16, 18. KSG-15 has the CTFA name cyclopentasiloxane/dimethicone/vinyl dimethicone crosspolymer. KSG-18 has the INCI name phenyl trimethicone/dimethicone/phenyl vinyl dimethicone crossoplymer. Silicone elastomers may also be purchased from Grant Industries under the Gransil trademark. Also suitable are silicone elastomers having long chain alkyl substitutions such as lauryl dimethicone/vinyl dimethicone crosspolymers supplied by Shin Etsu under the tradenames KSG-31, KSG-32, KSG-41, KSG-42, KSG-43, and KSG-44. Cross-linked organopolysiloxane elastomers useful in the present invention and processes for making them are further described in U.S. Pat. No. 4,970,252 to Sakuta et al., issued Nov. 13, 1990; U.S. Pat. No. 5,760,116 to Kilgour et al., issued Jun. 2, 1998; U.S. Pat. No. 5,654,362 to Schulz, Jr. et al. issued Aug. 5, 1997; and Japanese Patent Application JP 61-18708, assigned to Pola Kasei Kogyo KK, each of which are herein incorporated by reference in its entirety.

2. Emulsifying Silicone Elastomers

Also suitable as the viscosity enhancing synthetic polymer are various types of crosslinked silicone surfactants that are often referred to as emulsifying elastomers. They are typically prepared as set forth above with respect to the section "silicone elastomers" except that the silicone elastomers will contain at least one hydrophilic moiety such as polyoxyalkylenated groups. Typically these polyoxyalkylenated silicone elastomers are crosslinked organopolysiloxanes that may be obtained by a crosslinking addition reaction of diorganopolysiloxane comprising at least one hydrogen bonded to silicon and of a polyoxyalkylene comprising at least two ethylenically unsaturated groups. In at least one embodiment, the polyoxyalkylenated crosslinked organo-polysiloxanes are obtained by a crosslinking addition reaction of a diorganopolysiloxane comprising at least two hydrogens each bonded to a silicon, and a polyoxyalkylene comprising at least two ethylenically unsaturated groups, optionally in the presence of a platinum catalyst, as described, for example, in U.S. Pat. Nos. 5,236,986 and 5,412,004, 5,837,793 and 5,811,487, the contents of which are incorporated by reference.

Polyoxyalkylenated silicone elastomers that may be used in at least one embodiment of the invention include those sold by Shin-Etsu Silicones under the names KSG-21, KSG-20, KSG-30, KSG-31, KSG-32, KSG-33; KSG-210 which is dimethicone/PEG-10/15 crosspolymer dispersed in dimethicone; KSG-310 which is PEG-15 lauryl dimethicone crosspolymer; KSG-320 which is PEG-15 lauryl dimethicone crosspolymer dispersed in isododecane; KSG-330 (the former dispersed in triethylhexanoin), KSG-340 which is a mixture of PEG-10 lauryl dimethicone crosspolymer and PEG-15 lauryl dimethicone crosspolymer.

Also suitable are polyglycerolated silicone elastomers like those disclosed in PCT/WO 2004/024798, which is hereby incorporated by reference in its entirety. Such elastomers include Shin-Etsu's KSG series, such as KSG-710 which is dimethicone/polyglycerin-3 crosspolymer dispersed in dimethicone; or lauryl dimethicone/polyglycerin-3 crosspolymer dispersed in a variety of solvent such as isododecane, dimethicone, triethylhexanoin, sold under the Shin-Etsu tradenames KSG-810, KSG-820, KSG-830, or KSG-840. Also suitable are silicones sold by Dow Corning under the tradenames 9010 and DC9011.

One preferred crosslinked silicone elastomer emulsifier is dimethicone/PEG-10/15 crosspolymer.

The composition may contain other ingredients, including but not limited to those set forth herein.

III. Other Ingredients

A. Oils

If the composition of the invention is in the emulsion or anhydrous form, it will generally comprise an oil phase. Suitable oils include silicones, esters, vegetable oils, synthetic oils, including but not limited to those set forth herein. The oils may be volatile or nonvolatile, and are in the form of a pourable liquid at room temperature. The term "volatile" means that the oil has a measurable vapor pressure, or a vapor pressure of at least about 2 mm. of mercury at 20° C. The term "nonvolatile" means that the oil has a vapor pressure of less than about 2 mm. of mercury at 20° C.

1. Volatile Oils (a). Volatile Silicones

Suitable volatile oils that may be used in the compositions of the invention generally have a viscosity ranging from about 0.5 to 5 centistokes 25° C. and include linear silicones, cyclic silicones, branched silicones, paraffinic hydrocarbons, or mixtures thereof.

Cyclic silicones are of the general formula:

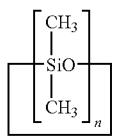

where n=3-6.

Linear volatile silicones in accordance with the invention have the general formula:

where n=0, 1, 2, 3, 4, or 5, preferably 0, 1, 2, 3, or 4.

Branched volatile silicones are generally of the formula:

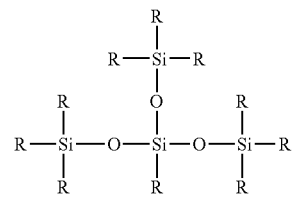

wherein R is $C_{1-4}$ alkyl, preferably methyl.

Linear and cyclic volatile silicones are available from various commercial sources including Dow Corning Corporation and General Electric. The Dow Corning volatile silicones are sold under the tradenames Dow Corning 244, 245, 344, and 200 fluids. These fluids comprise octamethylcyclotetrasiloxane, decamethylcyclopentasiloxane, dodecamethylcyclohexasiloxane and the like. Also suitable are linear volatile silicones such as hexamethyldisiloxane (viscosity 0.65 centistokes (abbreviated cst)), octamethyltrisiloxane (1.0 cst), decamethyltetrasiloxane (1.5 cst), dodecamethylpentasiloxane (2 cst) and mixtures thereof.

Suitable branched volatile silicones include methyl trimethicone, ethyl trimethicone, propyl trimethicone, butyl trimethicone and the like. Methyl trimethicone may be purchased from Shin-Etsu Silicones and has the trade name TMF 1.5, having the viscosity of 1.5 centistokes at 25° C.

(b). Volatile Paraffinic Hydrocarbons

Also suitable as the volatile oils are various straight or branched chain paraffinic hydrocarbons having 5, 6, 7, 8, 9, 10, 11, 12, 13, 14, 15, 16, 17, 18, 19, or 20 carbon atoms, more preferably 8 to 16 carbon atoms. Suitable hydrocarbons include pentane, hexane, heptane, decane, dodecane, tetradecane, tridecane, and $C_{8-20}$ isoparaffins as disclosed in U.S. Pat. Nos. 3,439,088 and 3,818,105, both of which are hereby incorporated by reference in their entireties for all purposes. Preferred volatile paraffinic hydrocarbons have a molecular weight of 70-225, preferably 160 to 190 and a boiling point range of 30 to 320, preferably 60 to 260° C., and a viscosity of less than about 10 cst. at 25° C. Such paraffinic hydrocarbons are available from EXXON under the ISOPARS trademark, and from the Permethyl Corporation. Suitable $C_{12}$ isoparaffins are manufactured by Permethyl Corporation under the tradename Permethyl 99A. Various $C_{16}$ isoparaffins commercially available, such as isohexadecane (having the tradename Permethyl R), are also suitable.

2. Non-Volatile Oils

A variety of nonvolatile oils are also suitable for use in the cosmetic compositions of the invention. The nonvolatile oils generally have a viscosity of greater than about 5 to 10 centistokes at 25° C., and may range in viscosity up to about 1,000,000 centipoise at 25° C. Examples of nonvolatile oils include, but are not limited to:

(a). Esters

Suitable esters are mono-, di-, and triesters. The composition may comprise one or more esters selected from the group, or mixtures thereof.

(i). Monoesters

Monoesters are defined as esters formed by the reaction of a monocarboxylic acid having the formula R—COOH, wherein R is a straight or branched chain saturated or unsaturated alkyl having 2 to 45 carbon atoms, or phenyl; and an alcohol having the formula R—OH wherein R is a straight or branched chain saturated or unsaturated alkyl having 2-30 carbon atoms, or phenyl. Both the alcohol and the acid may be substituted with one or more hydroxyl groups. Either one or both of the acid or alcohol may be a "fatty" acid or alcohol, and may have from about 6 to 30 carbon atoms, more preferably 12, 14, 16, 18, or 22 carbon atoms in straight or branched chain, saturated or unsaturated form. Examples of monoester oils that may be used in the compositions of the invention include hexyl laurate, butyl isostearate, hexadecyl isostearate, cetyl palmitate, isostearyl neopentanoate, stearyl heptanoate, isostearyl isononanoate, steary lactate, stearyl octanoate, stearyl stearate, isononyl isononanoate, and so on.

(ii). Diesters

Suitable diesters are the reaction product of a dicarboxylic acid and an aliphatic or aromatic alcohol or an aliphatic or aromatic alcohol having at least two substituted hydroxyl groups and a monocarboxylic acid. The dicarboxylic acid may contain from 2 to 30 carbon atoms, and may be in the straight or branched chain, saturated or unsaturated form. The dicarboxylic acid may be substituted with one or more hydroxyl groups. The aliphatic or aromatic alcohol may also contain 2 to 30 carbon atoms, and may be in the straight or branched chain, saturated, or unsaturated form. Preferably, one or more of the acid or alcohol is a fatty acid or alcohol, i.e. contains 12-22 carbon atoms. The dicarboxylic acid may also be an alpha hydroxy acid. The ester may be in the dimer or trimer form. Examples of diester oils that may be used in the compositions of the invention include diisotearyl malate, neopentyl glycol dioctanoate, dibutyl sebacate, dicetearyl dimer dilinoleate, dicetyl adipate, diisocetyl adipate, diisononyl adipate, diisostearyl dimer dilinoleate, diisostearyl fumarate, diisostearyl malate, dioctyl malate, and so on.

(iii). Triesters

Suitable triesters comprise the reaction product of a tricarboxylic acid and an aliphatic or aromatic alcohol or alternatively the reaction product of an aliphatic or aromatic alcohol having three or more substituted hydroxyl groups with a monocarboxylic acid. As with the mono- and diesters mentioned above, the acid and alcohol contain 2 to 30 carbon atoms, and may be saturated or unsaturated, straight or branched chain, and may be substituted with one or more hydroxyl groups. Preferably, one or more of the acid or alcohol is a fatty acid or alcohol containing 12 to 22 carbon atoms. Examples of triesters include esters of arachidonic, citric, or behenic acids, such as triarachidin, tributyl citrate, triisostearyl citrate, tri $C_{12-13}$ alkyl citrate, tricaprylin, tricaprylyl citrate, tridecyl behenate, trioctyldodecyl citrate, tridecyl behenate; or tridecyl cocoate, tridecyl isononanoate, and so on.

Esters suitable for use in the composition are further described on pages 2679-2688 of the C.T.F.A Cosmetic Ingredient Dictionary and Handbook, Eleventh Edition, 2006, which is hereby incorporated by reference in its entirety.

3. Hydrocarbon Oils

It may be desirable to incorporate one or more nonvolatile hydrocarbon oils into the composition. Suitable nonvolatile hydrocarbon oils include paraffinic hydrocarbons and olefins, preferably those having greater than about 20 carbon atoms. Examples of such hydrocarbon oils include $C_{24-28}$ olefins, $C_{30-45}$ olefins, $C_{20-40}$ isoparaffins, hydrogenated polyisobutene, polyisobutene, polydecene, hydrogenated polydecene, mineral oil, pentahydrosqualene, squalene, squalane, and mixtures thereof. In one preferred embodiment such hydrocarbons have a molecular weight ranging from about 300 to 1000 Daltons.

4. Glyceryl Esters of Fatty Acids

Synthetic or naturally occurring glyceryl esters of fatty acids, or triglycerides, are also suitable for use in the compositions. Both vegetable and animal sources may be used. Examples of such oils include castor oil, lanolin oil, $C_{10-18}$ triglycerides, caprylic/capric/triglycerides, sweet almond oil, apricot kernel oil, sesame oil, camelina sativa oil, tamanu seed oil, coconut oil, corn oil, cottonseed oil, linseed oil, ink oil, olive oil, palm oil, illipe butter, rapeseed oil, soybean oil, grapeseed oil, sunflower seed oil, walnut oil, and the like.

Also suitable are synthetic or semi-synthetic glyceryl esters, such as fatty acid mono-, di-, and triglycerides which are natural fats or oils that have been modified, for example, mono-, di- or triesters of polyols such as glycerin. In an example, a fatty ($C_{12-22}$) carboxylic acid is reacted with one or more repeating glyceryl groups. glyceryl stearate, diglyceryl diiosostearate, polyglyceryl-3 isostearate, polyglyceryl-4 isostearate, polyglyceryl-6 ricinoleate, glyceryl dioleate, glyceryl diisotearate, glyceryl tetraisostearate, glyceryl trioctanoate, diglyceryl distearate, glyceryl linoleate, glyceryl myristate, glyceryl isostearate, PEG castor oils, PEG glyceryl oleates, PEG glyceryl stearates, PEG glyceryl tallowates, and so on.

5. Nonvolatile Silicones

Nonvolatile silicone oils, both water soluble and water insoluble, are also suitable for use in the composition. Such silicones preferably have a viscosity ranging from about 10 to 800,000 cst, preferably 20 to 200,000 cst at 25° C. Suitable water insoluble silicones include amine functional silicones such as amodimethicone; phenyl substituted silicones such as bisphenylhexamethicone, trimethylsiloxyphenyl dimethicone, phenyl trimethicone, or polyphenylmethylsiloxane; dimethicone, dimethicone substituted with $C_{2-30}$ alkyl groups such cetyl dimethicone.

Nonvolatile silicones may have the following general formula:

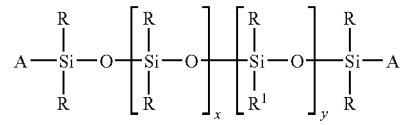

wherein R and R' are each independently $C_{1-30}$ straight or branched chain, saturated or unsaturated alkyl, phenyl or aryl, trialkylsiloxy, and x and y are each independently 0-1,000,000; with the proviso that there is at least one of either x or y, and A is alkyl siloxy endcap unit. Preferred is where A is a methyl siloxy endcap unit; in particular trimethylsiloxy, and R and R' are each independently a $C_{1-30}$ straight or branched chain alkyl, phenyl, or trimethylsiloxy, more preferably a $C_{1-22}$ alkyl, phenyl, or trimethylsiloxy, most preferably methyl, phenyl, or trimethylsiloxy, and resulting silicone is dimethicone, phenyl dimethicone, diphenyl dimethicone, phenyl trimethicone, or trimethylsiloxyphenyl dimethicone. Other examples include alkyl dimethicones such as cetyl dimethicone, and the like wherein at least one R is a fatty alkyl ($C_{12}$, $C_{14}$, $C_{16}$, $C_{18}$, $C_{20}$, or $C_{22}$), and the other R is methyl, and A is a trimethylsiloxy endcap unit, provided such alkyl dimethicone is a pourable liquid at room temperature. Phenyl trimethicone can be purchased from Dow Corning Corporation under the tradename 556 Fluid. Trimethylsiloxyphenyl dimethicone can be purchased from Wacker-Chemie under the tradename PDM-1000. Cetyl dimethicone, also referred to as a liquid silicone wax, may be purchased from Dow Corning as Fluid 2502, or from DeGussa Care & Surface Specialties under the tradenames Abil Wax 9801, or 9814.

6. Fluorinated Oils

Various types of fluorinated oils may also be suitable for use in the compositions including but not limited to fluorinated silicones, fluorinated esters, or perfluropolyethers. Particularly suitable are fluorosilicones such as trimethylsilyl endcapped fluorosilicone oil, polytrifluoropropylmethylsiloxanes, and similar silicones such as those disclosed in U.S. Pat. No. 5,118,496 which is hereby incorporated by reference. Perfluoropolyethers include those disclosed in U.S. Pat. Nos. 5,183,589, 4,803,067, 5,183,588 all of which are hereby incorporated by reference, which are commercially available from Montefluos under the trademark Fomblin.

B. Surfactants

It may be desirable to include one or more surfactants in the composition in order to aid in dispersing particulates or other ingredients that may be present, or stabilize the emulsion if the composition is in the form of an emulsion. The surfactants may be silicone or organic. If present, the surfactant may range from about 0.001 to 30%, preferably from about 0.005 to 25%, more preferably from about 0.1 to 20% by weight of the total composition.

1. Silicone Surfactants

Suitable silicone surfactants include linear polyorganosiloxane polymers that have amphiphilic properties, for example contain hydrophilic radicals and lipophilic radicals. These silicone surfactants may be liquids or solids at room temperature.

(a). Dimethicone Copolyols or Alkyl Dimethicone Copolyols

One type of silicone surfactant that may be used is generally referred to as dimethicone copolyol or alkyl dimethicone copolyol. This surfactant is either a water-in-oil or oil-in-water surfactant having an Hydrophile/Lipophile Balance (HLB) ranging from about 2 to 18. Preferably the silicone surfactant is a nonionic surfactant having an HLB ranging from about 2 to 12, preferably about 2 to 10, most preferably about 4 to 6. The term "hydrophilic radical" means a radical that, when substituted onto the organosiloxane polymer backbone, confers hydrophilic properties to the substituted portion of the polymer. Examples of radicals that will confer hydrophilicity are hydroxy-polyethyleneoxy, hydroxyl, carboxylates, and mixtures thereof. The term "lipophilic radical" means an organic radical that, when substituted onto the organosiloxane polymer backbone, confers lipophilic properties to the substituted portion of the polymer. Examples of organic radicals that will confer lipophilicity are $C_{1-40}$ straight or branched chain alkyl, fluoro, aryl, aryloxy, $C_{1-40}$ hydrocarbyl acyl, hydroxy-polypropyleneoxy, or mixtures thereof.

One type of suitable silicone surfactant has the general formula:

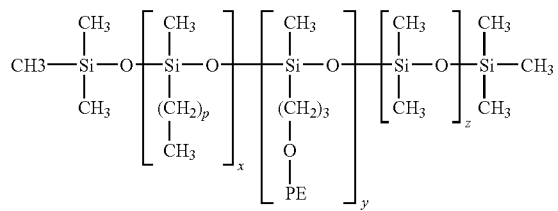

wherein p is 0-40 (the range including all numbers between and subranges such as 2, 3, 4, 13, 14, 15, 16, 17, 18, etc.), and PE is $(-C_2H_4O)_n-(-C_3H_6O)_b-H$ wherein a is 0 to 25, b is 0-25 with the proviso that both a and b cannot be 0 simultaneously, x and y are each independently ranging from 0 to 1 million with the proviso that they both cannot be 0 simultaneously. In one preferred embodiment, x, y, z, a, and b are such that the molecular weight of the polymer ranges from about 5,000 to about 500,000, more preferably from about 10,000 to 100,000, and is most preferably approximately about 50,000 and the polymer is generically referred to as dimethicone copolyol.

One type of silicone surfactant is wherein p is such that the long chain alkyl is cetyl or lauryl, and the surfactant is called, generically, cetyl dimethicone copolyol or lauryl dimethicone copolyol respectively.

In some cases the number of repeating ethylene oxide or propylene oxide units in the polymer are also specified, such as a dimethicone copolyol that is also referred to as PEG-15/PPG-10 dimethicone, which refers to a dimethicone having substituents containing 15 ethylene glycol units and 10 propylene glycol units on the siloxane backbone. It is also possible for one or more of the methyl groups in the above general structure to be substituted with a longer chain alkyl (e.g. ethyl, propyl, butyl, etc.) or an ether such as methyl ether, ethyl ether, propyl ether, butyl ether, and the like.

Examples of silicone surfactants are those sold by Dow Corning under the tradename Dow Corning 3225C Formulation Aid having the CTFA name cyclotetrasiloxane (and) cyclopentasiloxane (and) PEG/PPG-18 dimethicone; or 5225C Formulation Aid, having the CTFA name cyclopentasiloxane (and) PEG/PPG-18/18 dimethicone; or Dow Corning 190 Surfactant having the CTFA name PEG/PPG-18/18 dimethicone; or Dow Corning 193 Fluid, Dow Corning 5200 having the CTFA name lauryl PEG/PPG-18/18 methicone; or Abil EM 90 having the CTFA name cetyl PEG/PPG-14/14 dimethicone sold by Goldschmidt; or Abil EM 97 having the CTFA name bis-cetyl PEG/PPG-14/14 dimethicone sold by Goldschmidt; or Abil WE 09 having the CTFA name cetyl PEG/PPG-10/1 dimethicone in a mixture also containing polyglyceryl-4 isostearate and hexyl laurate; or KF-6011 sold by Shin-Etsu Silicones having the CTFA name PEG-11 methyl ether dimethicone; KF-6012 sold by Shin-Etsu Silicones having the CTFA name PEG/PPG-20/22 butyl ether dimethicone; or KF-6013 sold by Shin-Etsu Silicones having the CTFA name PEG-9 dimethicone; or KF-6015 sold by Shin-Etsu Silicones having the CTFA name PEG-3 dimethicone; or KF-6016 sold by Shin-Etsu Silicones having the CTFA name PEG-9 methyl ether dimethicone; or KF-6017 sold by Shin-Etsu Silicones having the CTFA name PEG-10 dimethicone; or KF-6038 sold by Shin-Etsu Silicones having the CTFA name lauryl PEG-9 polydimethylsiloxyethyl dimethicone.

2. Organic Surfactants (a). Organic Nonionic Surfactants

The composition may comprise one or more nonionic organic surfactants. Suitable nonionic surfactants include alkoxylated alcohols, or ethers, formed by the reaction of an alcohol with an alkylene oxide, usually ethylene or propylene oxide. Preferably the alcohol is either a fatty alcohol having 6 to 30 carbon atoms Examples of such ingredients include Steareth 2-100, which is formed by the reaction of stearyl alcohol and ethylene oxide and the number of ethylene oxide units ranges from 2 to 100; Beheneth 5-30 which is formed by the reaction of behenyl alcohol and ethylene oxide where the number of repeating ethylene oxide units is 5 to 30; Ceteareth 2-100, formed by the reaction of a mixture of cetyl and stearyl alcohol with ethylene oxide, where the number of repeating ethylene oxide units in the molecule is 2 to 100; Ceteth 1-45 which is formed by the reaction of cetyl alcohol and ethylene oxide, and the number of repeating ethylene oxide units is 1 to 45, and so on.

Other alkoxylated alcohols are formed by the reaction of fatty acids and mono-, di- or polyhydric alcohols with an alkylene oxide. For example, the reaction products of $C_{6-30}$ fatty carboxylic acids and polyhydric alcohols which are monosaccharides such as glucose, galactose, methyl glucose, and the like, with an alkoxylated alcohol. Examples include polymeric alkylene glycols reacted with glyceryl fatty acid esters such as PEG glyceryl oleates, PEG glyceryl stearate; or PEG polyhydroxyalkanotes such as PEG dipolyhydroxystearate wherein the number of repeating ethylene glycol units ranges from 3 to 1000.

Also suitable as nonionic surfactants are formed by the reaction of a carboxylic acid with an alkylene oxide or with a polymeric ether. The resulting products have the general formula: where RCO is the carboxylic ester radical, X is hydrogen or lower alkyl, and n is the number of polymerized alkoxy groups. In the case of the diesters, the two RCO-groups do not need to be identical. Preferably, R is a $C_{6-30}$ straight or branched chain, saturated or unsaturated alkyl, and n is from 1-100.

Monomeric, homopolymeric, or block copolymeric ethers are also suitable as nonionic surfactants. Typically, such ethers are formed by the polymerization of monomeric alkylene oxides, generally ethylene or propylene oxide. Such polymeric ethers have the following general formula: wherein R is H or lower alkyl and n is the number of repeating monomer units, and ranges from 1 to 500.

Other suitable nonionic surfactants include alkoxylated sorbitan and alkoxylated sorbitan derivatives. For example, alkoxylation, in particular ethoxylation of sorbitan provides polyalkoxylated sorbitan derivatives. Esterification of polyalkoxylated sorbitan provides sorbitan esters such as the polysorbates. For example, the polyalkyoxylated sorbitan can be esterified with $C_{6-30}$, preferably $C_{12-22}$ fatty acids. Examples of such ingredients include Polysorbates 20-85, sorbitan oleate, sorbitan sesquioleate, sorbitan palmitate, sorbitan sesquiisostearate, sorbitan stearate, and so on.

Certain types of amphoteric, zwitterionic, or cationic surfactants may also be used in the compositions. Descriptions of such surfactants are set forth in U.S. Pat. No. 5,843,193, which is hereby incorporated by reference in its entirety.

C. Humectants

It may also be desirable to include one or more humectants in the composition. If present, such humectants may range from about 0.001 to 25%, preferably from about 0.005 to 20%, more preferably from about 0.1 to 15% by weight of the total composition. Examples of suitable humectants include glycols in monomeric or polymeric form such as polyethylene and polypropylene glycols such as PEG 4-200, which are polyethylene glycols having from 4 to 200 repeating ethylene oxide units; as well as $C_{1-6}$ alkylene glycols such as propylene glycol, butylene glycol, pentylene glycol, ethylhexylglycerin, trehalose, trehalose dihydrdate, and the like. Preferably, the humectants used in the composition of the invention are $C_{1-6}$, preferably $C_{2-4}$ alkylene glycols, most particularly butylene glycol.

It may be desirable to include one or more botanical extracts in the compositions in addition to those botanical extracts that have kinase inhibitor activity. If so, suggested ranges are from about 0.0001 to 10%, preferably about 0.0005 to 8%, more preferably about 0.001 to 5% by weight of the total composition. Suitable botanical extracts include extracts from plants (herbs, roots, flowers, fruits, seeds) such as flowers, fruits, vegetables, and so on, including yeast ferment extract, padica pavonica extract, thermus thermophilis ferment extract, camelina sativa seed oil, boswellia serrata extract, olive extract, aribodopsis thaliana extract, acacia dealbata extract, acer saccharinum (sugar maple), acidopholus, acorns, aesculus, agaricus, agave, agrimonia, algae, aloe, citrus, brassica, cinnamon, orange, apple, blueberry, cranberry, peach, pear, lemon, lime, pea, seaweed, caffeine, green tea, chamomile, willowbark, mulberry, rosemary, poppy, and the like. Further specific examples include, but are not limited to, *Glycyrrhiza Glabra, Salix Nigra, Macrocycstis Pyrifera, Pyrus Malus, Saxifraga Sarmentosa, Vilis Vinifera, Moms Nigra, Scutellaria Baicalensis, Anthemis Nobilis, Salvia Sclarea, Citrus Medica Limonum, Panax Ginseng*, and mixtures thereof.

D. Particulate Materials

The compositions of the invention may contain particulate materials in the form of pigments, inert particulates, or mixtures thereof. If present, suggested ranges are from about 0.1-75%, preferably about 0.5-70%, more preferably about 0.1-65% by weight of the total composition. In the case where the composition may comprise mixtures of pigments and powders, suitable ranges include about 0.01-75% pigment and 0.1-75% powder, such weights by weight of the total composition.

1. Powders

The particulate matter may be colored or non-colored (for example white) non-pigmentatious powders. Suitable non-pigmentatious powders include bismuth oxychloride, titanated mica, fumed silica, spherical silica, polymethylmethacrylate, micronized teflon, boron nitride, acrylate copolymers, aluminum silicate, aluminum starch octenylsuccinate, bentonite, calcium silicate, cellulose, chalk, corn starch, diatomaceous earth, fuller's earth, glyceryl starch, hectorite, hydrated silica, kaolin, magnesium aluminum silicate, magnesium trisilicate, maltodextrin, montmorillonite, microcrystalline cellulose, rice starch, silica, talc, mica, titanium dioxide, zinc laurate, zinc myristate, zinc rosinate, alumina, attapulgite, calcium carbonate, calcium silicate, dextran, kaolin, nylon, silica silylate, silk powder, sericite, soy flour, tin oxide, titanium hydroxide, trimagnesium phosphate, walnut shell powder, or mixtures thereof. The above mentioned powders may be surface treated with lecithin, amino acids, mineral oil, silicone, or various other agents either alone or in combination, which coat the powder surface and render the particles more lipophilic in nature.

2. Pigments

The particulate materials may comprise various organic and/or inorganic pigments. The organic pigments are generally various aromatic types including azo, indigoid, triphenylmethane, anthroquinone, and xanthine dyes which are designated as D&C and FD&C blues, browns, greens, oranges, reds, yellows, etc. Organic pigments generally consist of insoluble metallic salts of certified color additives, referred to as the Lakes. Inorganic pigments include iron oxides, ultramarines, chromium, chromium hydroxide colors, and mixtures thereof. Iron oxides of red, blue, yellow, brown, black, and mixtures thereof are suitable.

E. Vitamins or Antioxidants

The compositions of the invention, may contain vitamins and/or coenzymes, as well as antioxidants. If so, 0.001-10%, preferably 0.01-8%, more preferably 0.05-5% by weight of the total composition are suggested. Suitable vitamins include ascorbic acid and derivatives thereof, the B vitamins such as thiamine, riboflavin, pyridoxin, panthenol, and so on, as well as coenzymes such as thiamine pyrophoshate, flavin adenin dinucleotide, folic acid, pyridoxal phosphate, tetrahydrofolic acid, and so on. Also Vitamin A and derivatives thereof are suitable. Examples are Vitamin A palmitate, acetate, or other esters thereof, as well as Vitamin A in the form of beta carotene. Also suitable is Vitamin E and derivatives thereof such as Vitamin E acetate, nicotinate, or other esters thereof. In addition, Vitamins D and K are suitable.

Suitable antioxidants are ingredients which assist in preventing or retarding spoilage. Examples of antioxidants suitable for use in the compositions of the invention are potassium sulfite, sodium bisulfite, sodium erythrobate, sodium metabisulfite, sodium sulfite, propyl gallate, cysteine hydrochloride, butylated hydroxytoluene, butylated hydroxyanisole, and so on.

F. Waxes

The composition may also contain waxes in addition to the synthetic polymeric viscosity enhancing agent. Such waxes may be synthetic, natural, or silicone based. If present such waxes may range from about 0.001-70%, preferably from about 0.005-65%, more preferably from about 0.01-50% by weight of the total composition. Suitable waxes include those having a melting point ranging from about 60 to 150° C., more preferably from about 65 to 100° C. Examples of such waxes include waxes made by Fischer-Tropsch synthesis, such as polyethylene or synthetic wax; or various vegetable waxes such as bayberry, candelilla, ozokerite, acacia, beeswax, ceresin, cetyl esters, flower wax, citrus wax, carnauba wax, jojoba wax, japan wax, polyethylene, microcrystalline, rice bran, lanolin wax, mink, montan, bayberry, ouricury, ozokerite, palm kernel wax, paraffin, avocado wax, apple wax, shellac wax, clary wax, spent grain wax, grape wax, and polyalkylene glycol derivatives thereof such as PEG6-20 beeswax, or PEG-12 carnauba wax; or fatty acids or fatty alcohols, including esters thereof, such as hydroxystearic acids (for example 12-hydroxy stearic acid), tristearin, tribehenin, oleic acid, stearic acid, and so on. Suitable silicone waxes include long chain alkyl dimethicones such as stearyl dimethicone, behenyl dimethicone, and so on.

G. Sunscreens

The composition of the invention may also contain chemical sunscreens which may be UVA or UVB absorbers.

(1). UVA Chemical Sunscreens

If desired, the composition may comprise one or more UVA sunscreens. The term "UVA sunscreen" means a chemical compound that blocks UV radiation in the wavelength range of about 320 to 400 nm. Preferred UVA sunscreens are dibenzoylmethane compounds having the general formula

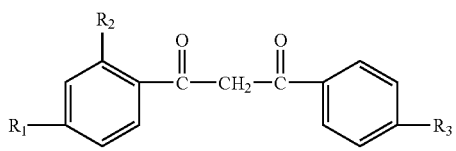

wherein $R_1$ is H, OR and NRR wherein each R is independently H, $C_{1-20}$ straight or branched chain alkyl; $R_2$ is H or OH; and $R_3$ is H, $C_{1-20}$ straight or branched chain alkyl.

Preferred is where $R_1$ is OR where R is a $C_{1-20}$ straight or branched alkyl, preferably methyl; $R_2$ is H; and $R_3$ is a $C_{1-20}$ straight or branched chain alkyl, more preferably, butyl.

Examples of suitable UVA sunscreen compounds of this general formula include 4-methyldibenzoylmethane, 2-methyldibenzoylmethane, 4-isopropyldibenzoylmethane, 4-tert-butyldibenzoylmethane, 2,4-dimethyldibenzoylmethane, 2,5-dimethyldibenzoylmethane, 4,4'diisopropylbenzoylmethane, 4-tert-butyl-4'-methoxydibenzoylmethane, 4,4'-diisopropylbenzoylmethane, 2-methyl-5-isopropyl-4'-methoxydibenzoymethane, 2-methyl-5-tert-butyl-4'-methoxydibenzoylmethane, and so on. Particularly preferred is 4-tert-butyl-4'-methoxydibenzoylmethane, also referred to as Avobenzone. Avobenzone is commercial available from Givaudan-Roure under the trademark Parsol 1789, and Merck & Co. under the tradename Eusolex 9020.

Other types of UVA sunscreens include dicamphor sulfonic acid derivatives, such as ecamsule, a sunscreen sold under the trade name Mexoryl™, which is terephthalylidene dicamphor sulfonic acid, having the formula:

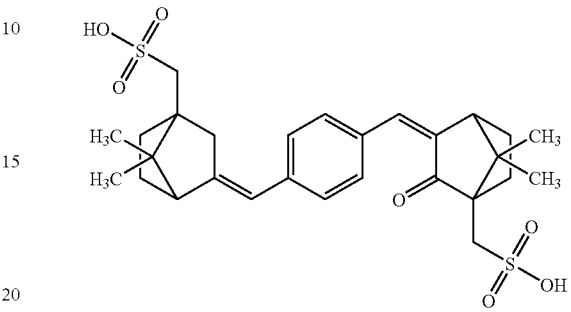

The composition may contain from about 0.001-20%, preferably 0.005-5%, more preferably about 0.005-3% by weight of the composition of UVA sunscreen.

(2). UVB Chemical Sunscreens

The term "UVB sunscreen" means a compound that blocks UV radiation in the wavelength range of from about 290 to 320 nm. A variety of UVB chemical sunscreens exist including alpha-cyano-beta,beta-diphenyl acrylic acid esters as set forth in U.S. Pat. No. 3,215,724, which is hereby incorporated by reference in its entirety. One particular example of an alpha-cyano-beta,beta-diphenyl acrylic acid ester is Octocrylene, which is 2-ethylhexyl 2-cyano-3,3-diphenylacrylate. In certain cases the composition may contain no more than about 110% by weight of the total composition of octocrylene. Suitable amounts range from about 0.001-10% by weight. Octocrylene may be purchased from BASF under the tradename Uvinul N-539.

Other suitable sunscreens include benzylidene camphor derivatives as set forth in U.S. Pat. No. 3,781,417, which is hereby incorporated by reference in its entirety. Such benzylidene camphor derivatives have the general formula:

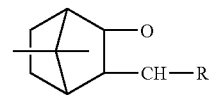

wherein R is p-tolyl or styryl, preferably styryl. Particularly preferred is 4-methylbenzylidene camphor, which is a lipid soluble UVB sunscreen compound sold under the tradename Eusolex 6300 by Merck.

Also suitable are cinnamate derivatives having the general formula:

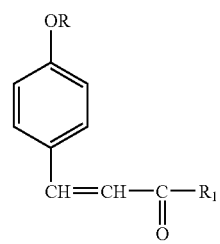

wherein R and $R_1$ are each independently a $C_{1-20}$ straight or branched chain alkyl. Preferred is where R is methyl and $R_1$ is a branched chain $C_{1-10}$, preferably $C_8$ alkyl. The preferred compound is ethylhexyl methoxycinnamate, also referred to as Octoxinate or octyl methoxycinnamate. The compound may be purchased from Givaudan Corporation under the tradename Parsol MCX, or BASF under the tradename Uvinul MC 80. Also suitable are mono-, di-, and triethanolamine derivatives of such methoxy cinnamates including diethanolamine methoxycinnamate. Cinoxate, the aromatic ether derivative of the above compound is also acceptable. If present, the Cinoxate should be found at no more than about 3% by weight of the total composition.

Also suitable as UVB screening agents are various benzophenone derivatives having the general formula:

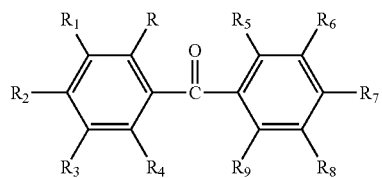

wherein R through $R_9$ are each independently H, OH, $NaO_3S$, $SO_3H$, $SO_3Na$, Cl, R", OR" where R" is $C_{1-20}$ straight or branched chain alkyl Examples of such compounds include Benzophenone 1, 2, 3, 4, 5, 6, 7, 8, 9, 10, 11, and 12. Particularly preferred is where the benzophenone derivative is Benzophenone 3 (also referred to as Oxybenzone), Benzophenone 4 (also referred to as Sulisobenzone), Benzophenone 5 (Sulisobenzone Sodium), and the like. Most preferred is Benzophenone 3.

Also suitable are certain menthyl salicylate derivatives having the general formula:

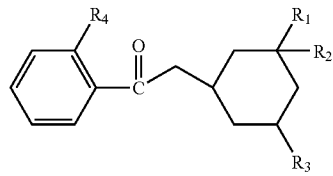

wherein $R_1$, $R_2$, $R_3$, and $R_4$ are each independently H, OH, $NH_2$, or $C_{1-20}$ straight or branched chain alkyl. Particularly preferred is where $R_1$, $R_2$, and $R_3$ are methyl and $R_4$ is hydroxyl or $NH_2$, the compound having the name homomenthyl salicylate (also known as Homosalate) or menthyl anthranilate. Homosalate is available commercially from Merck under the tradename Eusolex HMS and menthyl anthranilate is commercially available from Haarmann & Reimer under the tradename Heliopan. If present, the Homosalate should be found at no more than about 15% by weight of the total composition.

Various amino benzoic acid derivatives are suitable UVB absorbers including those having the general formula:

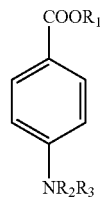

wherein $R_1$, $R_2$, and $R_3$ are each independently H, $C_{1-20}$ straight or branched chain alkyl which may be substituted with one or more hydroxy groups. Particularly preferred is wherein $R_1$ is H or $C_{1-8}$ straight or branched alkyl, and $R_2$ and $R_3$ are H, or $C_{1-8}$ straight or branched chain alkyl. Particularly preferred are PABA, ethyl hexyl dimethyl PABA (Padimate O), ethyldihydroxypropyl PABA, and the like. If present Padimate O should be found at no more than about 8% by weight of the total composition.

Salicylate derivatives are also acceptable UVB absorbers. Such compounds have the general formula: wherein R is a straight or branched chain alkyl, including derivatives of the above compound formed from mono-, di-, or triethanolamines. Particular preferred are octyl salicylate, TEA-salicylate, DEA-salicylate, and mixtures thereof.

Generally, the amount of the UVB chemical sunscreen present may range from about 0.001-45%, preferably 0.005-40%, more preferably about 0.01-35% by weight of the total composition.

If desired, the compositions of the invention may be formulated to have a certain SPF (sun protective factor) values ranging from about 1-70, preferably about 2-65, most preferably about 5-55. Calculation of SPF values is well known in the art.

The invention also comprises a method for whitening skin by treating skin with the compositions of the invention. The term "whitening skin" means to inhibit the production of melanin in skin by inhibiting tyrosinase production, or by blocking other pathways that contribute to formation of melanin in skin. In skin whitening, the compositions of the invention may be applied to skin once, twice, or more per day, preferably in the morning and evening, such as in the form of day or night creams, or facial toners or serums. The compositions will be applied over a period of days to achieve the desired results.

The invention also comprises a method of treating skin for improvement by applying the compositions of the invention. The term "treating skin for improvement" means treating various cosmetic conditions such as dry skin, skin laxity, fine lines and wrinkles, redness, irritation, acne, or similar conditions. In this case the composition may be applied from one to four times a day in the form of skin creams or lotions, serums, toners, and the like.

The invention also comprises a method for treating uneven skin pigmentation, mottling, age spots, or dermatological conditions such as roseacea, hyperkeratinization, eczema, etc. by applying the compositions of the invention one or more times per day. The compositions may be applied in the form of skin creams, lotions, toners, astringents, serums, facial cleansers, or color cosmetics such as foundation, blush, and the like.

The invention will be further described in connection with the following examples which are set forth for the purposes of illustration only.

EXAMPLE 1

The extract of *Trametes Versicolor* was compared with various other extracts for its efficacy in whitening skin. The following test compositions were prepared:

| Ingredient | Spiralex XP formula | Glucose Oxidase Enzyme formula | Trametes Extract formula | Salicylic Acid formula | Kojic Acid formula |
|---|---|---|---|---|---|
| | w/w % | | | | |
| Satin Finish III-9* | 50.00 | 50.00 | 50.00 | 50.00 | 50.00 |
| Tristat SDHA | 0.10 | 0.10 | 0.10 | 0.10 | 0.10 |
| EDETA/NA2 | 0.14 | 0.14 | 0.14 | 0.14 | 0.14 |
| Glycerine 99% | 4.00 | 4.00 | 4.00 | 4.00 | 4.00 |
| Aluminum starch octenyl-succinate | 1.00 | 1.00 | 1.00 | 1.00 | 1.00 |
| Water | QS | QS | QS | QS | QS |
| Carbopol 1382** | 0.30 | 0.30 | 0.30 | 0.30 | 0.30 |
| Carbopol 980*** | 0.35 | 0.35 | 0.35 | 0.35 | 0.35 |
| Xanthan Gum | 0.20 | 0.20 | 0.20 | 0.20 | 0.20 |
| Triethanol-Amine | 0.10 | 0.10 | 0.10 | 0.10 | 0.10 |
| Spiralex XP**** | 2.00 | | | | |
| Glucose oxidase enzyme | | 0.02 | | | |
| Glucose substrate | | 0.36 | | | |
| Freeze dried *Tramates Versicolor* Extract | | | 1.00 | | |
| Salicylic acid | | | | 2.00 | |
| Kojic acid | | | | | 2.00 |

*Water/phenyl trimethicone/cyclomethicone/dimethiconol/phosphoglycerides/carbomer/triethanolamine
**Acrylates/C10-30 Alkyl Acrylate Crosspolymer
***Carbomer
****Hydrogenated starch hydrolysate and yeast extract Nine female volunteers age 18-45, with skin type I-II (Fitzpatrick, 1986) were recruited from a local population. Panelists had to be in normal health with no evidence of acute or chronic disease; dermatologic conditions such as sunburn, rashes, scratches, burn marks, and the like; or non-users of systemic or topical retinoids, anti-histamines or similar agents during the course of the study or two weeks prior to commencement. Distinct areas approximately 4 cm$^2$ were marked on the backs of panelists corresponding to the test materials and an additional one as the untreated control. Each panelist received twice the MED dose of UVB on each marked site. The source of radiation was a Xenon Arc Solar Simulator (150 Watts) with filters (mm UG-5) to allow UVB and UVA transmittance. Immediately after irradiation, the test materials were applied to the respective sites at a dose of 2 mg/cm$^2$ and allowed to dry for 10 minutes. Product treatment was continued once a day (excluding Sundays) for 18 days. Color measurements of the test sites were performed using a Minolta Chromameter on alternate days for 15 days after irradiation.

The results are illustrated in the bar graph below, and show that the composition containing *Trametes Versicolor* extract was the most effective in lightening skin when compared with compositions containing Hydrogenated starch hydrolysate and yeast extract, glucose oxidase enzyme, salicylic acid, and the standard whitening ingredient kojic acid.

EXAMPLE 2

Skin treatment compositions for face and body were prepared as follows:

| Ingredient | 1 | 2 | 3 | 4 | 5 |
|---|---|---|---|---|---|
| | w/w % | | | | |
| *Selaginella Tamariscina* (spike moss) extract | 0.004 | 0.004 | 0.002 | | |
| *Siegesbeckia Orientalis* extract/glycerin | | | | | 0.10 |
| *Astrocaryum murumuru* butter | | | | | 0.20 |
| Water/butylene glycol/*Glycine Soja* soybean) oil/retinol/Carbomer/tocopherol/*Acacia Senegal* gum/propylene glycol alginate | | | | | 1.00 |
| Polymethyl methacrylate | | | | | 2.25 |
| *Glycine Soja* (soybean) protein | | | | 0.20 | |
| Tocopheryl acetate | | | | | 0.10 |
| Bis-PEG-18 methyl ether dimethyl silane | | | | | 1.50 |
| Whey protein | | | | 0.50 | |
| Cholesterol/potassium sulfate | | | 0.20 | | |
| Potassium sorbate | | | | | 0.10 |
| Cetyl ricinoleate | | | | | 1.50 |
| Petrolatum | | | | | 2.00 |
| Cholesterol | | | 0.20 | 0.20 | |
| Wheat (*Triticum Vulgare*) bran extract/olive (*Olea Europaea*) extract | | | 0.20 | | |
| Propylene glycol dicaprate/*Helianthus Annus* (sun-Flower seed cake)/*Hordeum Vulgare* (barley) Extract/*Cucumis Sativus*/ (cucumber) fruit extract | 0.50 | 0.50 | | | |
| Di C12-15 alkyl fumarate | 3.00 | 3.00 | | | |
| Water/Disodium EDTA-copper | 0.001 | 0.002 | | 0.003 | |
| NDGA | 0.002 | 0.002 | 0.001 | | |
| Saccharide isomerate | 1.00 | 1.00 | | | |
| Caprylic/capric Myristic/Stearic trigly-Ceride | 4.00 | 4.00 | | | |
| Acetyl Glucosamine | 1.00 | 1.00 | 2.00 | 0.20 | |
| Butylene glycol/sea whip (*Gorgonian*) extract | | | | 0.10 | |
| *Betula Alba* (birch) extract/water/*Saccharomyces* lysate extract | | | | | 0.05 |
| Water/*Camellia Sinensis* (white tea) leaf extract/*Camellia Sinensis* (yellow) tea leaf extract/*Aspalanthus Linearis* | | | | | 0.05 |

-continued

| Ingredient | 1 | 2 | 3 | 4 | 5 |
|---|---|---|---|---|---|
| (red tea) extract/Saccharomyces lysate extract | | | | | |
| Camomilla Recutita (Matricaria) flower extract | | | 0.02 | | |
| Hexadecyl stearate | | | | 4.00 | |
| Adipic acid/neopentylglycol crosspolymer/hydroxypropyl methyl cellulose/VP/VA crosspolymer/amodimethicone | | | 5.00 | | |
| Phenethylresorcinol | | | 1.00 | | |
| Caprylyl glycol/phenoxyethanol/hexylene glycol | | | 0.50 | | 0.30 |
| Xanthan gum | | | | | 0.20 |
| Cetearyl alcohol/cetearyl glucoside | | | | | 2.50 |
| Tromethane | | | | | 0.40 |
| Acrylamide/sodium acryloyldimethyl-taurate copolymer/isohexadecane/Polysorbate-80 | | | | | 1.00 |
| Creatine | | | | | 0.0005 |
| Pentaerythrityl tetraoctanoate | | | | | 2.50 |
| Polyglyceryl-3 beeswax | | | | | 1.00 |
| Polyglycery-3 disiloxane dimethicone | | | 0.50 | | |
| Silica | | | | 7.00 | |
| Dimethicone/Polysilicone-11 | | 2.00 | | | |
| Vinyl dimethicone/methicone/silsesquioxane copolymer | | | 13.00 | | |
| Hydrogenated lecithin | | | | 1.00 | 1.50 |
| Ammonium acrylodimethyl-taurate/VP copolymer | 1.00 | 1.00 | 0.75 | | |
| Water/salicylic acid/sodium hydroxide/butylene glycol/Di-C12-18 alkyl dimonum chloride | | | | 2.50 | |
| Polysorbate 80 | | 0.90 | | | |
| Methyl paraben | 0.004 | 0.004 | | | |
| Cyclopentasiloxane/dimethicone | | | 6.00 | | |
| Dimethicone | | | 2.00 | 0.43 | |
| PEG-100 stearate | | | | 1.00 | |
| Glyceryl stearate/PEG-100 stearate | | | | 2.60 | |
| Glyceryl stearate | | | | | 1.00 |
| Molasses extract | | | | 0.02 | |
| Humulus Lupulus (hops) Extract/linoleic acid/linolenic acid | 0.010 | 0.010 | 0.005 | | |
| Rosemary extract | 0.004 | 0.004 | 0.002 | | |
| Molasses extract | 0.010 | 0.01 | | | |
| Adenosine phosphate | 0.002 | 0.002 | | 0.0004 | |
| Propylene glycol dicaprylate/Cucumis Melo (melon) fruit Extract/Persea Gratissima (avocado) oil/Cholesterol/Potassium sulfate | 0.20 | 0.20 | | 0.20 | |
| Phenoxyethanol | 0.8 | 0.86 | 0.505 | 0.50 | |
| Cyclopentasiloxane | | 2.00 | | | |
| Dimethicone crosspolymer-3/isododecane | | | 2.00 | | |
| Polysorbate 20 | | 0.20 | | | |
| Disodium EDTA | 0.05 | 0.05 | 0.20 | 0.05 | |
| Ethylhexyl glycerin | 0.80 | 0.80 | 0.30 | | 0.30 |
| Pentylene glycol | 0.50 | 0.10 | 1.00 | | |
| Water/Acetyl hexapeptide-8 | 0.10 | 0.10 | 1.00 | | 10.00 |
| Linoleic acid | 0.20 | 0.20 | 0.20 | | 0.20 |
| Butylene glycol | 3.70 | 3.70 | 3.00 | | 4.00 |
| Glyceryl polymathacrylate/PEG-8/Palmitoyl oligopeptide | | | | | 0.20 |
| Acetyl carnitine HCl | | | | | 0.0005 |
| Sodium RNA | | | | | 0.20 |
| Acrylates/C10-30 alkyl acrylate crosspolymer | | | | | 0.35 |
| Phenyl trimethicone | | | | | 1.00 |
| Sucrose | 1.00 | 1.00 | | | |
| Punica Granatum (pomegranate) Juice extract | 0.002 | 0.002 | 0.001 | | |
| Cyclodextrin/ethylbis-Iminomethylguaiacol Manganese chloride | 0.002 | 0.002 | 0.001 | | |
| Vitis Vinifera (grape) seed extract | 0.005 | 0.005 | 0.002 | | |
| Sodium acrylate/sodium acryloyldimethyltaurate copolymer/hydrogenated polydecene/Laureth-8 | 2.40 | 1.00 | | | |
| Citric acid | 0.10 | | | | |
| Pentaerythrityl tetraoctanoate | 2.00 | 2.00 | | | |
| Butylene glycol/Water/Oryza Sativa (rice) bran extract | 0.20 | 0.20 | | | |
| Caffeine | 0.20 | 0.20 | | | 0.20 |
| Citri Reticulatae peel extract | 0.002 | 0.002 | 0.001 | | |
| Morus Nigra (mulberry) root extract/Scutellaria Baicalensis extract, Vitis Vinifera (grape) extract | 0.50 | 0.50 | | | |
| Butylene glycol/Scutellaria Baicalensis root extract/Morus Bombycis root extract | | | | | 0.50 |
| Shea butter | 4.00 | 4.00 | | | |
| Sodium hyaluronate | 0.02 | 0.02 | | | 0.005 |
| Simmondsia Chinensis (jojoba) seed oil | | | | | 5.00 |
| Simethicone | 0.0002 | 0.0002 | 0.0001 | | 0.000005 |
| Malt extract | 0.05 | 0.05 | 0.15 | | 0.03 |
| Water/phospholipids/ascorbyl tocopheryl maleate/Rosmarinus Officianalis extract/NDGA/linoleic acid/ | | | | | 1.00 |

-continued

| Ingredient | w/w % | | | | |
|---|---|---|---|---|---|
| | 1 | 2 | 3 | 4 | 5 |
| linolenic acid | | | | | |
| Polygonum Cuspidatum root extract | 0.010 | 0.010 | 0.005 | | |
| *Polygonum Cuspidatum* root extract/water/ *Saccharomyces* lysate extract | | | 0.05 | | |
| Tetrahexadecyl ascorbate | | | | 0.10 | |
| Myristyl myristate | | | | 0.50 | |
| Phytantriol | | 0.50 | | | |
| Glycerin | 2.00 | 2.00 | | | 5.00 |
| *Trametes Versicolor* extract | 0.02 | 0.02 | 2.00 | | 0.04 |
| Hydrocotyl extract | | | | | 0.10 |
| Water | QS100 | QS100 | QS100 | QS100 | QS100 |

The compositions are prepared by combining the ingredients and mixing well.

While the invention has been described in connection with the preferred embodiment, it is not intended to limit the scope of the invention to the particular form set forth but, on the contrary, it is intended to cover such alternatives, modifications, and equivalents as may be included within the spirit and scope of the invention as defined by the appended claims.

What we claim is:

1. A method for lightening the color of uneven skin pigmentation, skin mottling, or age spots due to exposure to UV radiation comprising applying to the areas of skin exposed to UV radiation, at least once per day a topical composition comprising (a) at least one extract from *Trametes versicolor* in an amount sufficient to inhibit tyrosinase, and (b) at least one viscosity enhancing synthetic polymer for a period of time sufficient to cause the uneven skin pigmentation, skin mottling, or age spots to become lighter in color.

2. The method of claim 1 wherein the skin mottling, or age spots are due to exposure to UVB radiation.

3. The method of claim 2 wherein the skin has been exposed to UVB radiation and the composition is applied to the uneven skin pigmentation, skin mottling or age spots in the form of a skin cream or lotion.

4. The method of claim 2 wherein the viscosity enhancing synthetic polymer is carbomer or acrylates C10-30 alkyl acrylates crosspolymer.

5. The method of claim 4 wherein the *Trametes versicolor* extract is also a skin moisturizer.

6. The method of claim 2 wherein the extract is from *Trametes versicolor* and the composition additionally comprises whey protein.

7. The method of claim 6 wherein the *Trametes versicolor* extract is a tyrosinase inhibitor and a skin moisturizer.

8. The method of claim 6 wherein the *Trametes versicolor* extract is obtained by extraction with water, alkanols, or volatile organic solvents.

9. The method of claim 6 wherein the *Trametes versicolor* extract is present from 0.00001-40% by weight of the total composition.

10. The method of claim 6 wherein the composition is applied in the form of a skin cream or lotion.

11. The method of claim 10 wherein the composition additionally comprises one or more humectants.

12. The method of claim 1 wherein the skin has been exposed to UVB radiation and the composition is applied one or more times a day for at least 18 days in the form of a skin cream or lotion, toner, facial cleanser, serum, or color cosmetic composition and the treated areas become lighter in color by at least 15 days after first treatment.

13. The method of claim 12 wherein the skin has been exposed to both UVA and UVB radiation.

14. The method of claim 1 wherein the extract is *Trametes versicolor* obtained by extraction of the *Trametes* plant material with water, alkanols, or volatile organic solvents.

15. The method of claim 14 wherein the extract is present at 0.00001-40% by weight of the total composition.

16. The method of claim 15 wherein the composition additionally comprises one or more botanical extracts.

17. The method of claim 16 wherein the composition additionally contains one or more botanical extracts derived from herbs, roots, flowers, fruit, or seeds.

18. The method of claim 1 wherein the composition consists essentially of:
   a tyrosinase-inhibiting effective amount of *Trametes versicolor*; and
   a viscosity enhancing synthetic polymer selected from carbomer Acrylates C10-30 alkylacrylates crosspolymer and mixtures thereof.

* * * * *